United States Patent [19]

Inazuka et al.

[11] 4,219,570

[45] Aug. 26, 1980

[54] INSECT REPELLENTS AND A METHOD OF REPELLING INSECTS

[75] Inventors: Shinichi Inazuka, Yokohama; Shigekatsu Tsuchiya, Yokosuka, both of Japan

[73] Assignee: Ajinomoto Company, Incorporated, Tokyo, Japan

[21] Appl. No.: 11,991

[22] Filed: Feb. 14, 1979

[30] Foreign Application Priority Data

Feb. 20, 1978 [JP]  Japan .................................. 53-18296

[51] Int. Cl.$^2$ ............................................ A01N 9/24
[52] U.S. Cl. .................................... 424/343; 424/308; 424/331; 424/333; 424/339; 424/341; 424/346; 424/DIG. 10
[58] Field of Search ............... 424/DIG. 10, 346, 308, 424/343, 333, 331, 339, 341

[56] References Cited

U.S. PATENT DOCUMENTS 3,929,912  12/1975  Hervert ................................. 568/736

OTHER PUBLICATIONS

Roth et al., "Tests of Repellents Against Tabanids", ARS Bull. #33-2 (1954), p. 1-4.
Chemical Abstracts, vol. 61 (1964), p. 6242a.
Chemical Abstracts, vol. 82 (1975), p. 154641q.
Chemical Abstracts, vol. 82 (1975), p. 124969k.
Chemical Abstracts, vol. 58 (1963), p. 11185c.

Primary Examiner—V. D. Turner
Attorney, Agent, or Firm—Oblon, Fisher, Spivak, McClelland & Maier

[57] ABSTRACT

A class of α-branched chain alkyl or alkenyl substituted benzene compounds have excellent repelling activities against numerous noxious insects.

10 Claims, No Drawings

INSECT REPELLENTS AND A METHOD OF REPELLING INSECTS

This invention relates to insect repellents and a method of repelling insects.

The term "insect repellent" as defined herein includes insect feeding deterrent and egg-laying deterrent besides its literal sense.

A number of insect repellents have been developed hitherto. For example, N,N-dimethyl m-toluamide has been practically used as mosquito repellent. Camphor, naphthalene and p-dichlorobenzene have been practically used for repelling insects which attack clothing. Although not practically used yet, isoboldine is known to be effective against Prodenia litura, demissine to be effective against *Scolytus multistriatus.* 4-Methylphenol and 4-ethylphenol were reported to be effective as warning pheromones against Blattella. Also, G. Kajimoto et al have reported about repellency of some antioxidants for foods, hydroquinone, BHA (mixture of 2-tert-butyl-4-hydroxyanisole and 3-tert-butyl-4-hydroxyanisole) and BHT (2-6-ditert-butyl-4-methylphenol) against fly's laver and cockroach (Nutrition and Food 14, 378–383 (1962)). However, there is very little example of having studied in details about insect repellency of compounds from their chemical structural aspects.

As a result of having tested about repellency of a number of aromatic compounds against various kinds of obnoxious insects in a view of mutual relation between chemical structure and repellent activity for purpose of developing insect repellents having high safety and suitability for practical use, we have now found that a certain class of α-branched chain hydrocarbon substituted benzene compounds have more effective repellent activity and broad insect repelling spectrum over those in the prior art.

The class of substituted benzene compounds as proved valuable insect repellents are represented by the following general formula.

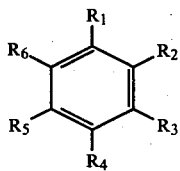

wherein $R_1$ is α-branched chain alkyl or alkenyl radical having 3 to 6 carbon atoms, $R_2$, $R_4$ and $R_6$ are each hydrogen, hydroxyl, lower alkyl, lower alkoxyl, lower aliphatic acyl, lower alkoxycarbonyl, hydroxyl substituted lower alkyl, aldehyde or halogen, but all of $R_2$, $R_4$ and $R_6$ are not hydrogen, $R_3$ and $R_5$ are each hydrogen, methyl, ethyl, hydroxyl substituted lower alkyl or aldehyde.

The term "lower" as defined herein is meant radical containing 1 to 4 carbon atoms.

The chemical structural characteristics of the present repellents are the following.

1. $R_1$ should be α-branched carbon chain to exhibit the desired repellent effect. Compounds where $R_1$ is substituted by other carbon chain such as straight chain alkyl or vinyl radical have little repellent action. Also, substitution of $R_1$ by other radical than carbon chain, such as carboxyl, amino, aldehyde or hydroxyl radical causes little or no insect repellency.

2. $R_2$, $R_4$ and $R_6$ which are located at ortho- and para-positions to $R_1$ are equivalent one another in repellent effect and act positively in repellency. Compounds where all of $R_2$, $R_4$ and $R_6$ are hydrogen have little repellent power, whereas compounds where at least one of $R_2$, $R_4$ and $R_6$ is hydroxyl, lower alkoxyl, lower aliphatic acyl, lower alkoxycarbonyl, hydroxyl substituted lower alkyl, aldehyde or halogen have excellent repellent activity. But, the repellent activity is greatly decreased when at least one of $R_2$, $R_4$ and $R_6$ is carboxyl, amino or N-substituted amino radical.

3. $R_3$ and $R_5$ which are located at meta position to $R_1$ are equivalent in repellent activity each other but do not take part or act negatively in repellency in contrary to the tendency of substituents being located at ortho and para positions. When relatively large molecules such as tert-butyl radical is introduced into that position, repellency activity is greatly decreased because of its steric hindrance to the chemical receptor such as antenna of insect. Preferably $R_3$ and $R_5$ are each hydrogen, methyl, ethyl, hydroxyl substituted lower alkyl or aldehyde radical.

More specifically, examples of α-branched chain $C_3$–$C_6$ alkyl or alkenyl radical represented by $R_1$ include isopropyl, sec-butyl, tert-butyl, sec-amyl, tert-amyl, sec-hexyl, tert-hexyl and isopropenyl radicals. Examples of lower alkyl radical in $R_2$, $R_4$ and $R_6$ include methyl, ethyl, n-propyl, isopropyl, n-butyl, isobutyl, sec-butyl and tert-butyl radicals. Examples of lower alkoxyl radical include methoxy, ethoxy, propoxy, butoxy, isobutoxy and tert-butoxy radicals. Examples of lower aliphatic acyl radical include acetyl radical. Examples of lower alkoxycarbonyl radical include methoxycarbonyl, ethoxycarbonyl and butoxycarbonyl radicals. Examples of hydroxyl substituted lower alkyl radical include hydroxymethyl, 2-hydroxyethyl, 1-hydroxyethyl and 1-hydroxypropyl radical. And, examples of halogen atom are fluorine, chlorine, bromine and iodine.

Representative examples of compounds which may be used as insect repellents in the present invention are the following.

o-cumenol, p-cumenol, 2-tert-butylphenol, 4-tert-butylphenol, 2-sec-butylphenol, 4-sec-butylphenol, 4-sec-amylphenol, 2-tert-amylphenol, 4-tert-amylphenol, 4-sec-hexylphenol, 4-tert-hexylphenol, 2,4-dihydroxycumene, 2,6-dihydroxycumene, 2,4-dihydroxy-1-tert-butylbenzene, 2,6-dihydroxy-1-tert-butylbenzene, o-cymene, m-cymene, p-cymene, 2,3-dimethylcumene, 2,6-dimethylcumene, 2,4,6-trimethylcumene, 3,4,5-trimethylcumene, 1,4-dimethylisopropylbenzene, 4-ethylcumene, 1,4,-di-tert-butylbenzene, 4-isobutyl-1-tert-butylbenzene, 4-sec-butyl-1-tert-butylbenzene, 4-sec-amyltoluene, 4-tert-amyltoluene, 6-isopropyl-m-cresol, 6-tert-butyl-m-cresol, 6-tert-amyl-m-cresol, 4-isopropyl-m-cresol, 4-tert-butyl-m-cresol, 4-tert-amyl-m-cresol, 6-isopropyl-o-cresol, 6-tert-butyl-o-cresol, 6-sec-butyl-o-cresol, 6-tert-amyl-o-cresol, 4-isopropyl-o-cresol, 4-tert-butyl-o-cresol, 4-tert-amyl-o-cresol, 2-isopropyl-p-cresol, 2-tert-butyl-p-cresol, 3-methyl-6-isopropylanisole, 3-methyl-6-tert-butylanisole, 3-methyl-6-tert-amylanisole, 2-methyl-4-isopropylanisole, 2-methyl-4-tert-butylanisole, 2-isopropyl-4-methylanisole, 2-tert-butyl-4-methylanisole, 3-ethyl-6-t- butylanisole, 3,6-di-tert-butylphenol, 2-tert-butyl-5-sec-butylphenol, 1-tert-butyl-2,3,4-trimethoxybenzene, 1-tert-butyl-2,4,6-trimethoxybenzene, 1,2,3-trimethyl-5-tert-butylbenzene, 1-tert-butyl-2-isobutylbenzene, 1-sec-butyl-2,4-dimethoxybenzene, 2,6-dihydroxy-p-cymene, 2-(2-hydroxyethyl)-p-cymene, 3-(3-hydroxypropyl)-p-cymene, 2-ethyl-p-cymene, 2,6-dimethoxy-p-cymene, 2-propenyl-p-cymene, 4-tert-butyl-m-cymene, 4-isopropylbenzaldehyde, 4-tert-butylbenzaldehyde, 4-tert-amylbenzaldehyde, 4-sec-butylbenzaldehyde, 2-tert-butyl-benzaldehyde, 2-tert-4,6-dimethylbutylbenzaldehyde, 2,3,4-trimethyl-6-tert-butylbenzaldehyde, 4-isopropylbenzylaldehyde, 4-sec-butyl-benzaldehyde, 4-tert-butylbenzylalcohol, 4-tert-amylbenzylalcohol, 2-isopropylbenzylalcohol, 2-tert-butyl-benzylalcohol, 2,6-dimethyl-4-tert-butylbenzylalcohol, 2,3-dimethyl-5-tert-butylbenzylalcohol, 2-hydroxy-5-tert-butyl-benzylalcohol, 2-hydroxy-3-methyl-5-butylbenzylalcohol, 2-isobutoxy-5-tert-butylbenzylalcohol, 2-methoxy-5-sec-butyl-benzylalcohol, 4-tert-butyl-α-methylbenzylalcohol, 2-methyl-5-tert-butylbenzylalcohol, 4-isopropenyl-α,α-dimethylbenzylalcohol, 4-tert-butyl-α,α-dimethylbenzylalcohol, 2,4-dihydroxy-5-tert-butylbenzylalcohol, 4-isopropylacetophenone, 4-tert-butylacetophenone, methyl 2-isopropylbenzoate, ethyl 2-tert-butyl-benzoate, methyl 4-isopropylbenzoate, methyl 4-tert-butylbenzoate, methyl 4-isopropyl-3-hydroxybenzoate, methyl 4-tert-butyl-3-hydroxybenzoate, 4-tert-butyl-3-hydroxybenzaldehyde, 4-chlorocumene, 2-chlorocumene, 2,4-dichlorocumene, 2,5-dichlorocumene, 2-chloro-p-cymene, 4-chloro-m-cymene, 1,4-di-tert-butyl-2-brombenzene, 1-bromo-4-tert-butylbenzene, 1-fluoro-2-bromo-4-tert-butylbenzene, methyl 2-tert-butyl-5-chlorobenzoate, 2-tert-butyl-6-chloro-p-cresol, 6-isopropenyl-m-cresol, 2,5-di-tert-butyl-p-cresol and the like.

The present repellents are mainly effective against Pterygota and Acari. For example, they are effective against either of imago (irrespective of male and female) and larva of the following insects: Thysanura (e.g. Lepismatidae), Orthoptera (e.g. Locustidae, Blattidae, Gryllidae), Isoptera (e.g. Phinolermmitidae), Hemiptera (e.g. Delphacidae, Deltocephalidae, Aphididae, Coccidae and Pentatomidae), Lepidoptera (e.g. Noctuidae, Pyralididae, Carposinidae and Tortricidae), Diptera (e.g. Culicidae, Muscidae, Tabanidae, Trypetidae, Simuliidae, Sarcophagidae and Agromyzidae), Coleoptera (e.g. Bruchidae, Dermestidae, Ptinidae, Chrysomllidae and Anobiidae), Hymenoptera (e.g. Formicidae), Acari (e.g. Ixodides and Tetranychidae).

Compounds of the aforementioned general formula may be directly applied as insect repellents singly or in admixture of two or more components. Or, it may also be applied in any formulation such as solutions, dispersions, oil agents, emulsifiable concentrates, wettable powders, dusts, granules, aerosols, fumigants or gels with suitable liquid carriers, solid carriers, emulsifying agents, dispersing agents, suspending agents, spreader, penetrating agents, wetting agents, stabilizing agents, gelling agents, steam fog accelerator. Examples of liquid carriers include water, alcohols (e.g. methyl alcohol, ethyl alcohol, ethylene glycol, cyclodextrin), ketones (e.g. acetone, methyl ethyl ketone), ethers (e.g. dioxane, tetrahydrofuran, methyl cellosolve), aliphatic hydrocarbons (e.g. gasoline, kerosene, lamp oil, n-paraffin), aromatic hydrocarbons (e.g. benzene, toluene, xylene, solvent naphtha), organic bases (e.g. pyridine), halogenated hydrocarbons (e.g. chloroform, carbon tetrachloride), acid amides (e.g. dimethylformamide), esters (e.g. ethyl acetate, butyl acetate, fatty acid glyceride), nitriles (e.g. acetonitrile), sulfur compounds (e.g. dimethylsulfoxide) and mixture thereof. Examples of solid carriers include botanical powders (such as soy bean powder, tobacco powder, wheat flour, wood powder); mineral powders (such as clays which include kaolin, bentonite and acid clay); talcs which include talc powder, pyrophyllite, silicas which include diatomaceous earth and mica; alumina, powdery sulfur and active charcoal. These powdery materials may be employed singly or in mixtures of two or more components.

Suitable emulsifiers, spreader and penetrants are soaps, higher alcohol sulfates, alkyl sulfonates, alkylaryl sulfonates, quaternary ammonium salts, fatty acid esters of oxyalkylamines, polyalkylene oxides and anhydrosorbitols.

As gelling agents, there may be employed agar, metal soaps, dibenzylidine sorbitol, N-acylamino acid esters, N-acylamino acid amides, amine salts of N-acylamino acids and 12-hydroxystearic acid. As steam fog accelerators, there may be employed any sublimative compound such as p-dichlorobenzene, camphor and trimer of isobutyraldehyde.

If necessary, casein, gelatin, starch, alginic acid, methyl cellosolve, polyvinyl alcohol, wood turpentine, richebran oil, sucrose, glucose, molasses and amino acids may also be added to the composition.

The repelling agents of the present invention may also be employed in admixture with insecticidal agents (e.g. organochlorine, organophosphorus compounds, carbamates and natural insecticides), synergic agents, other insect repelling agents, pigments, bactericides and fungicides.

As explained above, the present repellent can be directly applied to an area from which it is desirable to repel the insects by conventional methods wherein it is sprayed, fogged, scattered, brushed or heated to volatilize or otherwise it is placed in the form of paper piece, cloth piece impregnated with a small amount of it or in the form of microcapsules containing it and further heated to volatilize, whereby the damage from the insects may be efficiently controlled.

It is not necessary to pay particular attention for the amount applied of the present repellent, since the present repellent exhibits appreciable repellent effect even when applied in a very small amount. However, it is desirable to apply the present repellent so as to deposit from about 0.001 to about 1 mg. per $cm^2$ of surface area to be applied or so as to exist at concentration of from about 0.001 to about 1 p.p.m. in air when sprayed, scattered, fogged. Similar amount is applicable even in case where the present repellent is placed in the form of paper piece, cloth piece or microcapsule containing it or otherwise is further subjected to heating to volatilize it.

The following examples are intended to illustrate the advantages of the insect repellents of the present invention. However, it is not intended to limit the invention to the specific compounds and concentrations shown therein.

EXAMPLE 1

The evaluation of the repellent activity of compounds exemplified by the above formula against German cockroach (*Blattella germanica* Linné) was accomplished in the following manner.

German cockroaches, including adult males, females and nymphs were placed without food and water in a plastic box, 30 cm square by 10 cm deep. The inner lip of the box was coated with a thin layer of paraffin oil to prevent the insects' escape.

The cockroaches are in the habit of gathering in the corner of the box. A paper disc, 0.7 cm diameter by 0.04 cm thick, was treated immediately before the test by pipetting 0.02 ml of 1000, 100 and 10 p.p.m. solution of the inventive compound in acetone. After air-drying, the disc was placed in the corner of the box.

Repellency was judged by the cockroaches' behavior against the treated disc. The behavior of the compound having repellent activity the cockroaches scamper away from the disc. The activity rating scale used was as follows:
- —: no repellent activity
- ±: slightly repellent activity
- +: moderately repellent activity
- ++: good repellent activity Results are shown in Chart 1. Column 1 gives the name of the compound; column 2, the rate in terms of p.p.m. at which the compound was applied to the disc;

EXAMPLE 2

The evaluation of the repellent activity of compounds exemplified by the above formula against cockroach Periplaneta picea Shiraki was accomplished in the following manner.

The cockroaches, including each 20 adult males, females and nymphs were placed without food and water in a stainless steel box (30 cm×100 cm×20 cm). The inner lip of the box was coated with a thin layer paraffin oil to prevent the insect' escape. The box was covered by a plastic plate. Two shelters, 6.5 cm square by 1 cm deep, were placed in the corner of the box. The cockroaches were offered a choice of two shelters, one of which was treated immediately before the test with 0.5 ml of a solution of acetone containing 10 mg of the inventive compound on the entire inner surface. The cockroaches were counted after 24 hours in the shelters. Repellency was calculated by the formula:

$$\frac{\text{Untreated} - \text{treated}}{\text{Total}} \times 100 = \text{Percent repellency}$$

The activity rating scale used was follows:
- —: no repellent activity, percent repellency is below 60
- ±: slightly repellent activity, percent repellency is from 60 to 75
- +: good repellent activity, percent repellency is above 75 below 100
- ++: remarkable repellent activity, percent repellency is 100

Results are shown in Chart 2. Column 1 gives the name of the compound; column 2, the activity rating of the compound against the cockroaches.

EXAMPLE 3

The evaluation of the repellent activity of the compounds exemplified by the above formula against house fly, Musca domestica vicina Macquart, was accomplished in the following manner.

250 pairs house flies were placed in a plastic box (100 cm×100 cm×100 cm). Two 1-percent sugar water pots, one of which was 100 p.p.m. solution of the compound containing insecticide fenitrothion, were on the center of the box.

The killed house flies in the each pots are counted after 24 hours. Repellency was calculated by the formula:

$$\frac{\text{Untreated} - \text{Treated}}{\text{Untreated}} \times 100 = \text{Percent repellency}$$

The active rating scale used was as follows:
- —: no repellent activity, percent repellency is below 20
- ±: slightly repellent activity, percent repellency is from 20 to 50
- +: good repellent activity, percent repellency is above 50 below 100
- ++: remarkable repellent activity, percent repellency is 100.

Results are shown in Chart 2. Column 1 gives the name of the compound; column 3, the activity rating of the compound against house flies.

EXAMPLE 4

The evaluation of the repellent activity of compounds exemplified by the above formula against smaller brown planthopper, Laodelphex striatellus Fallen, and green rice leafhopper, Nephotettix cincticeps Uhler, was accomplished in the greenhouse in the following manner.

Repellent compositions were prepared by dissolving 10 mg. of the compound to be tested in 2 ml. of a solution of acetone containing 50 mg. of sulfonate non-ionic emulsifying agent and diluted to a volume of 20 ml. with water. The composition then contained 500 p.p.m. of repellent compound.

Five rice seeds (Nourin No. 8 variety) were planted in 4-inch clay pots and allowed to germinate. Four weeks from the day of planting, the test chemicals, compounded as described above, were sprayed on all leaf surfaces of the young rice plants and allowed to dry. The plants were then covered by a wire netting cylinder to prevent the insects' escape. Twenty female adults were placed into the cylinder. The adults sitting on leaves or stem of the plants were counted after 24 hours.

The percent repellency and the repellent active rating scale use were the same contents as house fly.

Results are shown in Chart 3. Column 1 gives the name of the compound, Column 2, the activity rating of the compound against smaller brown planthopper, Column 3, the activity rating of the compound against green rice leafhopper.

EXAMPLE 5

The evaluation of the feeding deterrent activity of compounds exemplified by the above formula against the larvaes of Tobacco cutworm and Diamond back moth, Prodenica litura Fabricius, was accomplished in the following manner. The composition contained 500 p.p.m. of repellent compound were prepared by the same method as Example 4. Leaf discs, 3 cm diameter, were punched out with a cork borer from leaves of kidney beans. The discs were immersed in the repellent compositions or in pure acetone as a control.

After air-drying, the discs were placed in polyethylene dishes with test larvae of Tobacco cutworm. The whole area of the control discs are usually eaten in one day, at which time the consumed area of all discs were measured by Dethrer's method, the consumed area of treated discs expressed as a percentage of the consumed area of control discs was used as an index of the antifeeding activity of the compound.

Feeding deterrent was calculated by the formula $$\frac{\text{Untreated} - \text{Treated}}{\text{Untreated}} \times 100 = \text{Percent feeding deterrent}$$

The antifeeding active rating scale used was follows:
- —: no antifeeding activity, percent feeding deterrent is below 20
- ±: slightly antifeeding activity, percent feeding deterrent is from 20 to 50.
- +: good antifeeding activity, percent feeding deterrent is above 50 below 100
- ++: remarkable antifeeding activity, percent feeding deterrent is 100.

Results are shown in Chart 4. Column 1 gives the name of the compound; Column 2, the activity rating of the compound against the larvae of Tobacco cutworm; Column 3, the activity rating of the compound against the larvae of Diamond back moth.

EXAMPLE 6

The evaluation of the repellent activity of compounds exemplified by the above formula against the larvae of small cabinet beetle, *Anthrenus verbascii*, was accomplished in the following manner.

Cloth discs, 2 cm diameter, were punched out with a cork borer from raw wool cloth. The discs were immersed in 10 p.p.m. and 1000 p.p.m. solutions of the inventive compound in acetone or in pure acetone as a control. After air-drying, the discs were placed in polyethylene dishes with 5 larvaes of the beetles.

Repellency was judged by the beetles, behavior against the treated disc. When a compound has no repellent activity, all larvaes are placed on the disc after 24 hours. But when a compound has repellent activity, no larvae is placed on the disc.

The activity rating scale used was as follows:
- —: no repellent activity
- ±: slightly repellent activity, some larvae are placed on the disc treated with 1000 p.p.m. solution.
- +: good repellent activity, no larvae is placed on the disc treated with 1000 p.p.m. solution or, some larvae are placed on the disc treated with 10 p.p.m. solution
- ++: remarkable repellent activity, no larvae is placed on the disc treated with 10 p.p.m. solution.

Results are shown in Chart 4. Column 1 gives the name of the compound; Column 4, the activity rating of the compound against the larvae of small cabinet beetle.

EXAMPLE 7

The evaluation of the repellent activity of compound against Green peach aphid, *Myzus persicae* Sulzer, and Carmine mite, *Tetranychus telarius* Linne, was accomplished in the following manner.

The composition contained 500 p.p.m. of repellent compound were prepared by the same method as Example 4.

Leaf discs, 3 cm. diameter were punched out with a cork borer from leaves of white rape or strawberry. The discs were immersed in the repellent compositions or in pure acetone as a control.

After air-drying, the discs were placed in polyethylene dishes with adults and nymphs of green peach aphid or carmine mite. Repellency and the activity rating scale were evaluated by the same method as Example 6.

Results are shown in Chart 4. Column 1 gives the name of the compound; Column 5, the activity rating of the compound against green peach aphid; Column 6, the activity rating of the compound against carmine mite.

EXAMPLE 8

The evaluation of egg-laying deterrent activity and ovicidal activity of compounds exemplified by the above formula against Azuki bean weevils, *Callosobruchus Chinensis* Linne, and Cowpea Weevil *Callosobruchus maculatus* Fabricius, was accomplished in the following manner. An Azuki bean was treated immediately before test with a solution contained 50 μg of the compound in acetone. Twenty pairs of weevils were then placed among 300 treated Azuki beans in the box 9 cm diameter by 5 cm deep. Total of eggs were counted after one week on the beans, and then, total of hatching eggs were counted after two weeks.

Egg-laying deterrent activity and ovicidal activity were calculated by the formulas $$\frac{(\text{Number of eggs on the untreated beans}) - (\text{Number of eggs on the treated beans})}{(\text{Number of eggs on the untreated beans})} =$$

Percent egg-laying deterrent activity $$\frac{(\text{Number of hatching eggs on the untreated beans}) - (\text{Number of hatching eggs on the treated beans})}{(\text{Number of hatching eggs on the untreated beans})} =$$

Percent ovicidal activity

The activity rating scale used follows:
- —: no activity, percent activity is below 30.
- ±: slight activity, percent activity is from 30 to 60.
- +: good activity, percent activity is above 60 below 100.
- ++: remarkable activity, percent activity is 100.

Results are shown in Chart 5. Column 1 gives the name of the compound; column 2, the egg-laying deterrent activity rating of the compound against Azuki bean weevils; column 3, the ovicidal activity rating of compound against Azuki bean weevils; column 4, the egg-laying deterrent activity rating of the compound against Cowpea Weevil; column 5, the ovicidal activity rating of the compound against Cowpea Weevils.

Chart 1

| Compound | Application Rate | | |
|---|---|---|---|
| | 1000 ppm | 100 ppm | 10 ppm |
| 2-Isopropyl phenol | ++ | + | — |
| 4-Isopropyl phenol | ++ | + | — |
| 2-sec-Butyl phenol | ++ | + | — |
| 4-sec-Butyl phenol | ++ | + | — |
| 2-tert-Butyl phenol | ++ | + | + |
| 4-tert-Butyl phenol | ++ | + | + |
| 2-sec-Amyl phenol | + | ± | — |
| 4-sec-Amyl phenol | + | ± | — |

Chart 1-continued

| Compound | Application Rate | | |
|---|---|---|---|
| | 1000 ppm | 100 ppm | 10 ppm |
| 2-tert-Amyl phenol | + | ± | − |
| 4-tert-Amyl phenol | + | ± | − |
| 2-sec-Hexyl phenol | + | ± | − |
| 4-sec-Hexyl phenol | + | ± | − |
| 4-Isopropyl toluene | ++ | ++ | − |
| 2-Isopropyl toluene | ++ | ++ | − |
| 4-Ethyl cumene | ++ | ++ | + |
| P-Diisopropyl benzene | ++ | ++ | ++ |
| 4-tert-Butyl cumene | ++ | ++ | ++ |
| Thymol | ++ | ++ | + |
| 4-Isopropyl-m-cresol | ++ | ++ | + |
| 3-Methyl-6-isopropyl anisole | ++ | + | + |
| 2,4-Dimethoxy cymene | ++ | + | + |
| 4-Isopropyl benzaldehyde | ++ | + | − |
| 2-Isopropyl benzaldehyde | ++ | + | − |
| 4-Isopropyl anisole | ++ | + | − |
| 4-Isopropyl acetophenone | ++ | + | − |
| 4-Isopropyl benzylalcohol | ++ | + | − |
| 3-Hydroxy-4-isopropyl anisole | ++ | ++ | + |
| Methyl 3-hydroxy-4-isopropyl benzoate | ++ | + | − |
| Ethyl 3-hydroxy-4-isopropyl benoate | ++ | + | − |
| 4-Isopropyl-o-xylene | ++ | − | − |
| 4-isopropyl-chlorobenzene | ++ | + | − |
| 2,5-Dichloro cumene | ++ | − | − |
| 3-Methyl-4-ethoxy cumene | ++ | + | − |
| 2-Methyl-4-ethyl cumene | ++ | + | − |
| 2-Ethyl-4-methyl cumene | ++ | + | − |
| 2-(2-Hydroxyethyl)-4-methyl cumene | ++ | + | − |
| 2-Hydroxy-3-isopropyl benzyl alcohol | ++ | + | − |
| 2-Methyl-5-isopropyl-p-hydroquinone | ++ | + | − |
| 2-Bromo-4-methyl-cumene | ++ | − | − |
| 2-Methyl-4-tert-butyl cumene | ++ | + | − |
| 2,4,5-Trimethyl cumene | ++ | + | − |
| 3,5-Diethyl cumene | ++ | − | − |
| 4-tert-Butyl toluene | ++ | + | − |
| 2-tert-Butyl toluene | ++ | + | − |
| 6-tert-Butyl-m-cresol | ++ | ++ | ++ |
| 1,4-Di-tert-butyl benzene | + | + | − |
| 2,5-Di-tert-butyl-4-hydroxy-benzyl alcohol | + | + | − |
| 4-tert-Butyl ethyl benzene | ++ | + | − |
| 3,5-Dimethyl-4-tert-butyl phenol | ++ | + | − |
| 3,5-Diisopropyl-4-tert-butyl phenol | + | + | − |
| 3-Hydroxy-6-tert-butyl anisole | ++ | + | − |
| 3-Hydroxy-6-tert-butyl toluene | ++ | ++ | + |
| 2-Hydroxy-3-tert-butyl toluene | ++ | + | − |
| 4-tert-Butyl benzaldehyde | ++ | + | − |
| 4-tert-Butyl benzoic acid methyl ester | ++ | + | − |
| 4-tert-Butyl benzylalcohol | ++ | ++ | + |
| 4-tert-Butyl benzoic acid isopropyl ester | ++ | ± | − |
| Methyl 3-methyl-6-tert-butyl benzoate | + | + | − |
| 4-tert-Butyl-o-xylene | ++ | + | − |
| 2,3-Dichloro-tert-butyl benzene | + | + | − |
| 4-tert-Butyl chloro benzene | + | + | − |
| 2-Ethoxy-5-tert-butyl toluene | ++ | + | − |
| 2-tert-Butyl-iso-butyl benzene | ++ | + | − |
| 1,2,3-Trimethyl-4-iodo-5-tert-butyl benzene | ++ | + | − |
| 1,2,3-Trimethyl-4-tert-butyl benzene | ++ | + | − |
| 1,3,5-Trimethoxy-6-tert-butyl benzene | ++ | ++ | + |
| 3,4-Dimethyl-6-tert-butyl benzene | ++ | + | − |
| 2,6-Dimethyl-4-tert-butyl benzyl alcohol | + | + | − |
| P-Cresol | − | − | − |
| P-Ethyl phenol | ± | − | − |
| P-n-Propyl phenol | − | − | − |
| Control P-n-Butyl phenol | − | − | − |
| P-iso-Butyl phenol | ± | − | − |
| P-n-Amyl phenol | − | − | − |
| Phenol | − | − | − |
| p-Hydroxy benzoic acid | − | − | − |
| p-Hydroquinone | − | − | − |
| p-(N-Dimethyl)-amino phenol | − | − | − |
| Control 4-Methoxy phenol | ± | − | − |
| Cumene | ± | − | − |
| m-Isopropyl phenol | ± | − | − |
| m-Isopropyl anisole | ± | − | − |
| 4-Isopropyl benzoic acid | − | − | − |
| 4-(N-Dimethyl)-amino cumene | − | − | − |
| Untreated | − | − | − |

Chart 2

| | Compound | Insect | Activity rating Cockroach | House fly |
|---|---|---|---|---|
| The present invention | p-Diisopropyl benzene | | ++ | + |
| | Thymol | | ++ | ++ |
| | 3-Methoxy-4-iso-propyl benzaldehyde | | ++ | ++ |
| | 6-tert-Butyl-m-cresol | | ++ | ++ |
| | 3-Methyl-6-tert-butyl anisole | | ++ | ++ |
| | 2,5-Dimethyl-4-tert-butyl anisole | | + | ++ |
| | 4-tert-Butyl resorcinol | | + | + |
| | 6-tert-Butyl-m-cresol | | ++ | ++ |
| | 3-Ethoxy-6-tert-amyl phenol | | + | ++ |
| | 3-Methyl-4-tert-butyl anisole | | + | + |
| | 4-sec-Amyl phenol | | + | + |
| Control | 2,6-Di-tert-butyl-4-methyl phenol | | − | − |
| | 3-tert-Butyl phenol | | ± | − |
| | p-Cresol | | − | − |
| | p-Ethyl phenol | | − | − |
| | Cumene | | − | − |
| | Untreated | | − | − |

Chart 3

| | Compound | Insect | Activity rating Smaller brown plant hopper | Green rice leaf hopper |
|---|---|---|---|---|
| The present invention | Thymol | | ++ | ++ |
| | 4-Isopropyl resorcinol | | ++ | ++ |
| | 3-Methyl-4-chloro cumene | | + | + |
| | 3,6-Dihydroxy-2-chloro-5-tert-butyl toluene | | ++ | ++ |
| | 3,6-Dihydroxy-2,5-di-tert-butyl toluene | | ++ | + |
| | 4-tert-Butyl-m-cresol | | ++ | + |
| | 6-tert-Butyl-m-cresol | | ++ | ++ |
| | 1,3,5-Trimethoxy-2-tert-butyl benzene | | + | + |
| | 4-tert-Amyl benzaldehyde | | + | + |
| | 4-tert-Amyl phenol | | + | + |
| Control | 2,6-Di-tert-butyl-p-cresol | | − | − |
| | p-tert-Butyl benzoic acid | | − | − |
| | p-Cresol | | − | − |
| | p-Ethyl phenol | | − | − |
| | m-Isopropyl phenol | | ± | − |
| | Untreated | | − | − |

Chart 4

| | Compound | Insect | Tabacco cutworm | Diamond back moth | Small cabinet beetle | Green peach aphid | Carmine mite |
|---|---|---|---|---|---|---|---|
| The present invention | 4-Isopropyl phenol | | + | + | ++ | + | + |
| | Thymol | | ++ | ++ | ++ | + | ++ |
| | 4-Ethyl cumene | | + | + | + | + | + |
| | 2,4-Dimethoxy cumene | | + | + | + | + | + |
| | 2-Ethyl-p-cymene | | + | + | + | + | + |
| | 4-Chloro-m-cymene | | + | ± | ++ | + | + |
| | 2-Isopropyl-5-iso-butyl phenol | | ++ | ++ | ++ | ++ | + |
| | 2,3,5-Trimethyl cumene | | + | + | + | + | + |
| | 3,5-Dimethyl-4-tert-butyl benzyl alcohol | | + | + | ++ | + | + |
| | 2-tert-Butyl-5-methoxy benzyl alcohol | | + | + | + | + | + |
| | 6-tert-Butyl-m-cresol | | ++ | + | ++ | + | + |
| | 3-Methyl-6-tert-butyl anisole | | + | + | ++ | + | + |
| | 1,4-Di-tert-butyl benzene | | ++ | ++ | ++ | + | + |
| | Methyl 3-methyl-4-tert-butyl benzoate | | + | + | + | + | + |
| | 4-tert-Butyl benzaldehyde | | ++ | ++ | ++ | + | + |
| | 2,3,4-Trimethyl-6-tert-butyl benzene ++ | | ++ | + | ++ | + | |
| | 4-sec-Butyl phenol | | + | + | ++ | + | + |
| | 4-sec-Butyl ethylbenzene | | + | + | + | + | + |
| | 1,3-Diemthoxy-sec-butyl benzene | | + | + | + | + | + |
| | 2-Methoxy-5-sec-butyl benzyl alcohol | | + | + | + | + | + |
| | 4-tert-Amyl-sec-butyl benzene | | + | + | ++ | ++ | ++ |
| | 4-ter-Amyl phenol | | + | + | + | + | + |
| | 4-tert-Amyl-o-cresol | | + | + | + | + | + |
| | 4-sec-Amyl phenol | | + | + | + | + | + |
| | 6-sec-Amyl-m-cresol | | + | + | + | + | + |
| | 4-sec-Amyl anisole | | + | + | + | + | + |
| | α,α-Dimethyl-4-sec-amyl-benzyl alcohol | | ++ | + | ++ | + | + |
| Control | 2,6-Di-tert-butyl-p-cresol | | − | − | − | − | − |
| | 4-tert-Butyl benzoic acid | | − | − | − | − | − |
| | 4-Isopropyl benzoic acid | | − | − | − | − | − |
| | m-Isopropyl phenol | | ± | − | ± | − | − |
| | m-Isopropyl anisole | | − | − | ± | − | − |
| | p-Cresol | | − | − | ± | − | − |
| | Untreated | | − | − | − | − | − |

Chart 4 header: Repellent Activity Rating

Chart 5

| | | Activity rating | | | |
|---|---|---|---|---|---|
| | Insect | Azuki bean weevil | | Cowpea weevil | |
| | Repellent | Egg-laying deterrent | Ovicidal | Egg-laying deterrent | Ovicidal |
| | Compound | | | | |
| The present invention | 6-tert-Butyl-m-cresol | ++ | ++ | ++ | ++ |
| | 3-Methyl-6-tert-butyl anisole | ++ | ++ | ++ | ++ |
| | 2,5-Di-tert-butyl-p-hydroquinone | ++ | + | ++ | ++ |
| | 1,4-Di-tert-Butyl benzene | + | + | + | + |
| | 4-tert-Butyl acetophenone | + | + | + | + |
| | 3,5-Dimethyl-4-tert-butyl phenol | + | + | + | + |
| | 3-Methyl-6-isopropyl benzaldehyde | + | + | + | + |
| | 1,4-Di-isopropyl benzene | ++ | + | ++ | + |
| | Thymol | ++ | ++ | ++ | ++ |
| | 4-Isopropyl benzyl alcohol | ++ | ++ | ++ | ++ |
| | 3-Methyl-6-tert-amyl benzyl alcohol | ++ | + | ++ | + |
| | 4-sec-Butyl chloro benzene | ++ | ++ | ++ | ++ |
| | 4-Isopropyl benzyl alcohol | ++ | ++ | ++ | ++ |
| Control | p-Cresol | − | − | − | − |
| | 4-Methoxy phenol | − | − | − | − |
| | 4-tert-Butyl benzoic acid | − | − | − | − |
| | m-Isopropyl phenol | ± | − | ± | − |
| | Untreated | − | − | − | − |

EXAMPLE 9

The emulsifilable composition was prepared by dissolving 10 parts of 6-tert-butyl-m-cresol, 5 parts of emulsifying agent polyoxyethylene oleate and 1 part of dipropylene glycol in 50 parts ethanol and 35 parts of water. The emulsifiable composition 100 times diluted by water was used against aphids.

EXAMPLE 10

A repellent insecticidal composition in an aerosol was prepared by mixing 10 parts of 3-methyl-6-isopropyl phenol, 1 part of insecticide malathion, 40 parts of ethanol, 5 parts of emulsifying agent polyoxy ethylene oleate, 5 parts of ethylene glycol, 39 parts of water and 20 parts of jetting gas.

EXAMPLE 11

A feeding deterrent composition against white arts was prepared by mixing 10 parts 4-tert-butyl-3-hydroxy-anisole, 30 parts of acetone, 1 part of spreader dioctyl sulfosuccinate, 1 part of emulsifiable agent polyoxy ethylene castor oil, 10 parts of ethanol and 48 parts of water.

EXAMPLE 12

A gel-type repellent composition was prepared by mixing 30 parts of 6-tert-butyl-m-cresol, 69 parts of ethanol, 1 parts of perfume and gelling agent dibenzylidene sorbitol.

EXAMPLE 13

A sublimated repellent composition was prepared by heating and mixing 5 parts of 2,5-diisopropyl phenol, 94.5 parts of sublimate isobutylaldehyde trimer and 0.5 parts of perfume.

EXAMPLE 14

A repellent composition in an aerosol against cockroaches was prepared by mixing 10 parts of 2,5-di-tert-butyl hydroquinone, 80 parts of normal paraffin, 9.5 parts of ethanol, 0.5 parts of perfume and 20 parts of Liquid propane gas.

What we claim is:

1. A method for repelling an insect which is a member of the order of Thysanura, Orthoptera, Isoptera, Hemiptera, Lepidoptera, Diptera, Coleoptera, Hymenoptera or Acari, which comprises: subjecting said insect to a repelling amount of at least one compound having the formula:

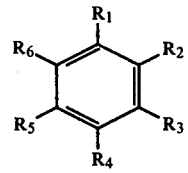

wherein $R_1$ is an α-branched chain alkyl or alkenyl radical having 3 to 6 carbon atoms; $R_2$, $R_4$ and $R_6$ are each hydrogen, hydroxyl, lower alkyl, lower alkoxyl, lower aliphatic acyl, lower alkoxycarbonyl, hydroxymethyl, 2-hydroxyethyl, 1-hydroxyethyl, 1-hydroxypropyl, —CHO or halogen, but all of $R_2$, $R_4$ and $R_6$ are not hydrogen; $R_3$ and $R_5$ are each hydrogen, methyl, ethyl, hydroxymethyl, 2-hydroxyethyl, 1-hydroxyethyl, 1-hydroxypropyl or —CHO; and when $R_4$ is hydroxy or 2-hydroxyethyl, all of $R_2$, $R_3$, $R_5$ and $R_6$ may not be hydrogen.

2. The method according to claim 1, wherein said compound is 6-tert-butyl-m-cresol.

3. The method according to claim 1, wherein said compound is 6-isopropyl-m-cresol.

4. The method according to claim 1, wherein said compound is 3-methyl-6-tert-butyl benzylalcohol.

5. The method according to claim 1, wherein said compound is a 3-lower alkyl-6-t-butylphenol.

6. The method according to claim 1, wherein the repelling amount of said compound ranges from about 0.001 to about 1 mg per $cm^2$.

7. The method according to claim 1, wherein the repelling amount of said compound ranges from about 0.001 to about 1 ppm in air.

8. The method according to claim 1, said compound is applied in combination with an inert carrier.

9. The method according to claim 1, wherein the insect repelled is of the order Diptera, Orthoptera, Lepidoptera or Coleoptera.

10. The method according to claim 1, wherein the insect repelled is of the order Hemiptera or Acari.

* * * * *